United States Patent [19]

Petrocine et al.

[11] Patent Number: 4,507,518

[45] Date of Patent: Mar. 26, 1985

[54] DEHYDRATION OF 2,5-DIMETHYL-2,5-HEXANEDIOL

[75] Inventors: David V. Petrocine, Saddle River; Ronald Harmetz, Randolph, both of N.J.

[73] Assignee: Penick Corporation, Lyndhurst, N.J.

[21] Appl. No.: 561,403

[22] Filed: Dec. 14, 1983

[51] Int. Cl.$^3$ .............................................. C07C 1/24
[52] U.S. Cl. .................................. 585/610; 585/609
[58] Field of Search ............... 585/601, 606, 609, 610, 585/627, 603, 604

[56] References Cited

U.S. PATENT DOCUMENTS

| | | | |
|---|---|---|---|
| 2,715,649 | 8/1955 | Hammond | 585/611 |
| 2,957,929 | 10/1960 | De La Mare | 585/610 |
| 3,692,743 | 9/1972 | Thompson | 585/604 |
| 3,857,903 | 12/1974 | Hagemeyer, Jr. et al. | 585/606 |
| 3,893,946 | 7/1975 | Weisang et al. | 585/611 |
| 4,147,736 | 4/1979 | Gokhberg et al. | 585/640 |
| 4,247,731 | 1/1981 | Wunder et al. | 585/640 |
| 4,296,266 | 10/1981 | Wunder et al. | 585/640 |
| 4,398,051 | 8/1983 | Araki et al. | 585/640 |
| 4,409,419 | 10/1983 | Prevedello et al. | 585/611 |
| 4,410,751 | 10/1983 | Shin et al. | 585/640 |

FOREIGN PATENT DOCUMENTS 2083071  3/1982  United Kingdom ............... 585/610

OTHER PUBLICATIONS

Tonkyn, R. G., "Synthesis of 2,5 Dimethyl-2,4 Hexadiene", Chem. Abstracts, vol. 71, (No. 19), 90707d.
Yuryev, et al., *J. Gen. Chem.*, USSR, 26, 293-296, (1956).

*Primary Examiner*—Delbert E. Gantz
*Assistant Examiner*—Anthony McFarlane
*Attorney, Agent, or Firm*—Stanley M. Parmerter

[57] ABSTRACT

This invention relates to an improved process for the dehydration of 2,5-dimethyl-2,5-hexanediol to give good yields of 2,5-dimethyl-2,4-hexadiene with a minimum of by-products. This is accomplished by heating 2,5-dimethyl-2,5-hexanediol with a montmorillonite clay catalyst, preferably in the presence of a lower aliphatic alcohol.

15 Claims, No Drawings

DEHYDRATION OF 2,5-DIMETHYL-2,5-HEXANEDIOL

FIELD OF THE INVENTION

This invention relates to a process for the preparation of 2,5-dimethyl-2,4-hexadiene by the catalytic dehydration of 2,5-dimethyl-2,5-hexanediol.

BACKGROUND OF THE INVENTION

The 2,5-dimethyl-2,4-hexadiene, prepared in accordance with the present invention, is a useful intermediate in the preparation of other organic compounds. It is especially useful as an intermediate in the synthesis of chrysanthemum monocarboxylic acid which is of importance in the manufacture of certain insecticides.

A number of methods for preparing 2,5-dimethyl-2,4-hexadiene are known. Among these known methods for preparing the diene are those which involve the use of 2,5-dimethyl-2,5-hexanediol, the starting compound used in the method of the present invention. Previous workers have reported various methods for converting the diol to the 2,4-hexadiene. These known methods, however, have certain deficiencies. Although the diol can be converted to the diene by heating with alumina, high temperatures are required and the product is contaminated with undesirable $C_8H_{14}$ isomers. The dehydration has been accomplished at somewhat lower temperatures by passing preheated vapors of the diol over a specially prepared catalyst that is obtained by heating alumina with phosphoric acid. Alternatively, a lower temperature acid catalyzed dehydration of the diol can be carried out in a slow reaction, but considerable amounts of undesired by-products are also formed. When the dehydration of the diol is carried out at high temperatures in the presence of a low acidity alumina and a lower aliphatic alcohol, the principal product is the 1,5-hexadiene rather than the 1,4-hexadiene.

It has now surprisingly been found, in accordance with the present invention, that under particular conditions 2,5-dimethyl-2,5-hexanediol can be converted to 2,5-dimethyl-2,4-hexadiene with good yields and selectivity. This method uses a different catalyst than those previously employed and when the reaction is carried out in the presence of a lower aliphatic alcohol, the desired 1,4-hexadiene is obtained in high yields.

The method of the present invention is accomplished at moderate temperatures in the presence of a simple catalyst and can be achieved rapidly in a continuous process. It also avoids the strong acidic conditions of various prior processes.

SUMMARY OF THE INVENTION

In accordance with this invention there is provided a process for the preparation of 2,5-dimethyl-2,4-hexadiene which comprises contacting 2,5-dimethyl-2,5-hexanediol with a montmorillonite clay catalyst at a temperature of from about 200° C. to about 300° C. The reaction is preferably carried out for a sufficient time to convert the majority of the 2,5-dimethyl-2,5-hexanediol to 2,5-dimethyl-2,4-hexadiene.

Also provided in accordance with this invention is a continuous process for the preparation of 2,5-dimethyl-2,4-hexadiene which comprises passing a mixture of 2,5-dimethyl-2,5-hexanediol and a lower aliphatic alcohol over a montmorillonite clay catalyst at a temperature of from about 200° C. to about 300° C.

DETAILED DESCRIPTION OF THE INVENTION

The process of this invention is carried out by contacting 2,5-dimethyl-2,5-hexanediol with a montmorillonite clay catalyst at a suitable temperature. Any form of the montmorillonite clay catalyst is suitable as long as it permits adequate contact with the diol and is in such a form that it can be readily separated from the reaction products. When the process is carried out as a continuous process, the particles of catalyst should be in a form that permits a reasonably rapid rate of flow of the reactant through the catalyst. It is convenient to use a catalyst which is in the form of spherical particles of a diameter of about 5 mm. Such a catalyst is available from the United Catalyst Company, Inc., Box 32370, Louisville, Ky., as Catalyst K-306.

The reaction temperature of the present process is usually in the range of from about 200° C. to about 300° C., preferably in the range of from about 240° C. to about 275° C. The temperature at which the process is carried out can be varied somewhat depending on the time in which the starting material is in contact with the catalyst.

The reaction can be carried out with or without a solvent present. However, it is preferred to use a solvent in the process of this invention since the solvent tends to minimize the formation of undesired by-products, and give higher yields of the desired 1,4-hexadiene.

The best yields of the 1,4-hexadiene are obtained when the process is carried out in the presence of a lower aliphatic, monohydric alcohol. The use of methanol as the lower aliphatic alcohol is preferred. Other lower aliphatic alcohols, for example, the monohydric aliphatic saturated alcohols having from 2 to 4 carbon atoms in the molecule, although not necessarily the equivalent of methanol in effectiveness, may, however, be used within the scope of the invention. The aliphatic alcohol employed may suitably consist of a mixture of two or more suitable monohydric alcohols. The lower aliphatic alcohol may be introduced in part, or in entirety, as a separate stream into the reaction zone or may be combined with the diol reactant before entering the reaction zone. In a preferred method of carrying out the process of the invention, the diol reactant is admixed with the monohydric alcohol solvent before introduction into the reaction zone.

The amount of the lower aliphatic monohydric alcohol employed in the practice of the invention may vary considerably. In general, the use of an alcohol such as methanol in sufficient amounts to give diol solutions varying from 0.2 to 20 molar are satisfactory.

Dehydration of the diol is carried out by contacting it with the catalyst for a sufficient time to convert the majority of the diol to the desired 1,4-hexadiene. As noted in the examples given below, this contact time will vary depending on the temperature at which the reaction is carried out and on the amount of the lower aliphatic alcohol present in the reaction mixture.

The following examples illustrate certain embodiments of the present invention. Unless otherwise stated, all proportions and percentages are provided on the basis of weight.

EXAMPLE 1

A reactor was constructed from a piece of glass tubing of 42-cm length and 2.7-cm internal diameter. This tube was enclosed in another glass tube of slightly larger diameter around which was wrapped a length of nichrome heating wire. The tubes were again enclosed in a slightly larger diameter glass tube which served as an air jacket. The tube ends were secured with tape to prevent laminar motion. The entrance to the reactor tube was fitted with a gas inlet tube and a steam-jacketed addition funnel. The exit of the tube reactor was attached to a 300-ml round bottomed flask fitted with a water-cooled condenser which in turn was fitted with a dry ice-isopropanol vapor trap and this in turn was fitted with a bubbler assembly which permitted observing of the rate of flow of the exit gas. An outlet at the bottom of the flask permitted removal of product.

The tube reactor was loaded with 150 g of montmorillonite clay spheres, Girdler No. 8583-S, obtained from the Chemical Products Division of Chemetron Corp., New York City. This same catalyst is now available from the United Catalyst Company, Inc., Box 32370, Louisville, Ky., as Catalyst K-306. Nitrogen was passed through the system as it was heated to the desired operating temperature by means of the nichrome wire. When the desired operating temperature was obtained as measured by a suitably placed thermocouple, a solution of 2,5-dimethyl-2,5-hexanediol in methanol was introduced into the reactor at a flow rate of from 0.5 to 4 ml/min. The 2,5-dimethyl-2,5-hexanediol was kept in solution by passing steam through the jacket of the addition funnel as needed. After the addition was complete, the system was flushed with nitrogen for several minutes. The product separated into two layers. The bulk of the product was in the lower layer while the upper layer was principally water and methanol.

The lower layer was analyzed by gas liquid partition chromatography (GLPC) according to the following procedure. About 100 mg of sample and 100 mg of anisole were weighed accurately in a vial. A standard was prepared by weighing accurately about 100 ml of authentic 2,5-dimethyl-2,4-hexadiene and 100 mg of anisole in a vial. One-microliter portions of the sample and the standard were injected in a Perkin-Elmer 881 gas chromatograph equipped with a flame ionization detector and an electronic integrator. The material was passed through a 150-ft Golay column coated with Apiezon. The oven was maintained at 80° C. The detector and the injector were at 150° C. Carrier gas was helium which has passed through the apparatus at a rate 3 to 4 ml/min and the split was made using a No. 29 needle. The make-up helium for the detector was added at a rate of about 26 ml/min. The amount of diene present was calculated by comparison of the peak areas of anisole and 2,4-diene and comparison with the standard of known concentration. The results of runs performed under various conditions are given in Table I. The yields are crude yields as measured by GLPC.

TABLE I

DEHYDRATION OF 2,5-DIMETHYL-2,5-HEXANEDIOL
(42 × 2.7 cm Reactor)

| Run No. | Molarity | Temp °C. | Flow Rate ml/min | 2,5-Dimethyl-2,4-Hexadiene % Yield | Comments |
|---|---|---|---|---|---|
| 1 | 2.5 | 250 | (a) | 64.5 | Also obtained 2.8% of the 1,5-diene |
| 2 | 6.0 | 260 | 1 | 67.4 | Also obtained 3.9% of the 1,5-diene |
| 3 | 25 | 275–295 | (a) | 70.9 | |
| 4 | No Solvent | 275 | (a) | 55.7 | Also obtained 9.6% of 2,2,5,5-tetramethyltetrahydrofuran |

(a) Not measured.

When molten 2,5-dimethyl-2,5-hexanediol was passed through the 42×2.7-cm reactor in the absence of methanol, at 200° C., 29.8% of 2,2,5,5-tetramethyltetrahydrofuran and 6.2% of 2,5-dimethyl-1,5-hexadiene were also formed giving only 49.6% of the desired 2,5-dimethyl-2,4-hexadiene. When the neat diol was passed through the reactor at 340° C., the majority of diene formed was 2,5-dimethyl-1,5-hexadiene and a considerable amount of polymerized material was produced. These runs indicate that montmorillonite clay is a suitable catalyst for the dehydration of 2,5-dimethyl-2,5-hexanediol and that the reaction gives the best yields when carried out in the presence of a lower aliphatic alcohol.

EXAMPLE 2

The general procedure of Example 1 was followed using a reactor prepared from a 60×2.7-cm glass column filled with 210 g of the montmorillonite catalyst. These runs employed a 5 molar solution of the diol in methanol and various reaction temperatures. The results, given in Table II, indicate that the reaction under these conditions is most efficient when carried out in the temperature range of from about 240° C. to 270° C.

TABLE II

DEHYDRATION OF 2,5-DIMETHYL-2,5-HEXANEDIOL
(60 × 2.7 cm Reactor)

| Run No. | Temp °C. | Flow Rate ml/min | 2,5-Dimethyl-2,4-Hexadiene % Yield | Comments |
|---|---|---|---|---|
| 5 | 170 | 1–2 | 14.8 | |
| 6 | 200 | 1–2 | 25.6 | |
| 7, 8, 9 | 240 | 1–2 | 57.8 to 91.4 | Average yield 72.2% |
| 10 | 270 | 1–2 | 75.5 | |
| 11 | 300 | 1–2 | 50.3 | |
| 12 | 330 | 1–2 | 29.9 | |

EXAMPLE 3

The general procedure of Example 1 was followed using the reactor of Example 2. Molarity of the methanol solution of diol, reaction temperature and flow rates were varied. The results given in Table III show the influences of these variables on product yield.

TABLE III

DEHYDRATION OF 2,5-DIMETHYL-2,5-HEXANEDIOL
(60 × 2.7 cm Reactor)

| Run No. | Molarity Methanol Solution | Temp °C. | Flow Rate ml/min | 2,5-Dimethyl-2,4-Hexadiene % Yield |
|---|---|---|---|---|
| 13 | 2.8 | 270 | 2.2 | 83.5 |
| 14 | 2.8 | 270 | 0.6 | 80.8 |
| 15 | 2.8 | 200 | 2.2 | 28.9 |
| 16 | 2.8 | 200 | 0.6 | 74.7 |
| 17 | 0.28 | 270 | 2.2 | 45.7 |
| 18 | 0.28 | 270 | 0.6 | 49.3 |
| 19 | 0.28 | 200 | 2.2 | 32.2 |

TABLE III-continued

DEHYDRATION OF 2,5-DIMETHYL-2,5-HEXANEDIOL
(60 × 2.7 cm Reactor)

| Run No. | Molarity Methanol Solution | Temp °C. | Flow Rate ml/min | 2,5-Dimethyl-2,4-Hexadiene % Yield |
|---|---|---|---|---|
| 20 | 0.28 | 200 | 0.6 | 55.0 |

Thus, it is apparent that there has been provided, in accordance with the invention, an improved process for the dehydration of 2,5-dimethyl-2,5-hexanediol to give 2,5-dimethyl-2,4-hexadiene in good yields with a minimum of by-products. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the conversion of 2,5-dimethyl-2,5-hexanediol into 2,5-dimethyl-2,4-hexadiene which comprises contacting 2,5-dimethyl-2,5-hexanediol with a montmorillonite clay catalyst at a temperature of from about 200° C. to about 300° C.

2. The process of claim 1 wherein the process is carried out in the presence of a lower aliphatic alcohol.

3. The process of claim 2 wherein the lower aliphatic alcohol is methanol.

4. The process of claim 1 wherein the process is carried out at a temperature of from about 240° C. to about 275° C.

5. The process of claim 2 wherein the process is carried out at a temperature of from about 240° C. to about 275° C.

6. The process of claim 3 wherein the process is carried out at a temperature of from about 240° C. to about 275° C.

7. The process of claim 1 wherein the process is carried out in a continuous manner.

8. The process of claim 7 wherein the catalyst is in the form of spherical particles.

9. A continuous process for the conversion of 2,5-dimethyl-2,5-hexanediol into 2,5-dimethyl-2,4-hexadiene which comprises passing a mixture of 2,5-dimethyl-2,5-hexanediol and a lower aliphatic alcohol over a montmorillonite clay catalyst at a temperature of from about 200° C. to about 300° C.

10. The process of claim 9 wherein the process is carried out at a temperature of from about 240° C. to about 275° C.

11. The process of claim 9 wherein the lower aliphatic alcohol is methanol.

12. The process of claim 10 wherein the lower aliphatic alcohol is methanol.

13. The process of claim 9 wherein the catalyst is in the form of spherical particles.

14. The process of claim 10 wherein the catalyst is in the form of spherical particles.

15. The process of claim 12 wherein the catalyst is in the form of spherical particles.

* * * * *